US005763608A

United States Patent [19]

Bhattacharya et al.

[11] Patent Number: 5,763,608
[45] Date of Patent: Jun. 9, 1998

[54] PROCESS FOR PREPARING PYRIMIDINE DERIVATIVES

[75] Inventors: Apurba Bhattacharya; Diane E. Allen, both of Corpus Christi, Tex.

[73] Assignee: Hoechst Celanese Corporation, Somerville, N.J.

[21] Appl. No.: 595,885

[22] Filed: Feb. 5, 1996

[51] Int. Cl.[6] .................. C07D 239/34; C07D 239/88

[52] U.S. Cl. .................. 544/319; 544/287; 544/253; 544/283; 544/279; 544/278; 544/254; 544/255; 544/256

[58] Field of Search .................. 544/319, 253, 544/287, 283, 279, 278, 254, 255, 256

[56] References Cited

PUBLICATIONS

Bormann, et al., Chem Ber., 1974, 107(1), pp. 270–277.

*Primary Examiner*—John M. Ford
*Attorney, Agent, or Firm*—James J. Mullen; Donald R. Cassady

[57] ABSTRACT

The present invention provides a process for preparing a 5,6-dihydro-3H-pyrimidin-4-one derivatives which comprises the steps of (a) dehydrating a N-acyl beta amino acid in the presence of a dehydration agent and an organic solvent for a sufficient period of time and under suitable temperature and pressure conditions to form an oxazone (b) adding a carboxylic acid and a primary amine salt of a carboxylic acid to said oxazone to form a mixture, (c) distilling azeotropically said mixture for a suitable period of time and under suitable temperature and pressure conditions to substantially remove said dehydration agent and said organic solvent, and (d) heating the product of step (c) for a sufficient period of time and under suitable temperature and pressure conditions to form said pyrimidin derivatives.

11 Claims, No Drawings

5,763,608

PROCESS FOR PREPARING PYRIMIDINE DERIVATIVES

BACKGROUND OF THE INVENTION

FIELD OF THE INVENTION

The present invention relates to a simple and efficient preparation of pyrimidin derivatives and a series of 4-quinazolone analogs from the corresponding amino acids such as anthranilic acids.

4-Quinazolone and their analogs belong to a class of potent, specific, non-peptide angiotensin II (AII) receptor antagonist, which provide a new method for the clinical treatment of hypertension. Angiotensin II, an octapeptide, formed by the action of angiotensin converting enzyme (ACE) on the decapeptide angiontensin I, is a powerful endogeneous vasoconstrictor. Existing methods for treating hypertension involve ACE inhibitors e.g. captopril and enalapril, which also affect hormones other than AII, causing unwanted side effects. In addition AII-antagonists play an important role in post myocardial infarction therapy, slowing AII-induced cardiac hypertrophy slowing the progression of heart failure, preventing post angioplasty restinosis, and in slowing the progress of renal disease. 4-Quinazolone and their analogs are also being developed as a new class of anti-tumor treatment. These discoveries have in turn led to an explosion of over 500 papers and patent applications by various pharmaceutical companies in this field as exemplified in Scheme 1.

Scheme 1

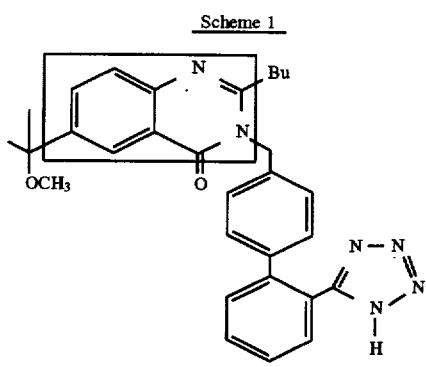

CL 329,167 (Lederle)

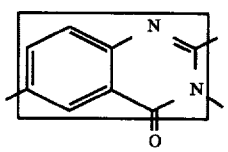

4(3H)-quinazolinone (Cynamid)

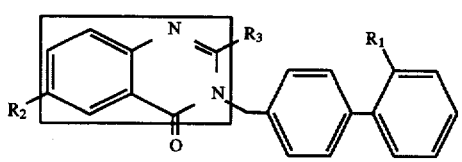

L-159,093; R₁ = CN₄H, R₂ = NHCON(CH₃)iPr, R₃ = n-Bu (Merck)

-continued
Scheme 1

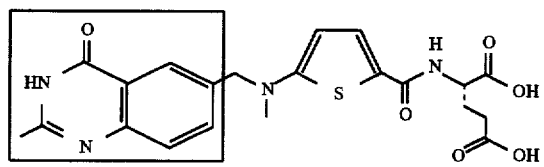

Tomudex™(Zeneca)

The current technology for the preparation of 4-quinazolones fall into the following categories.

1. Condensation of anthranilic acid with formamide (Niementowski's synthesis): Thermal condensation (fusion) of anthranilic acid with formamide produces 4-quinazolones.

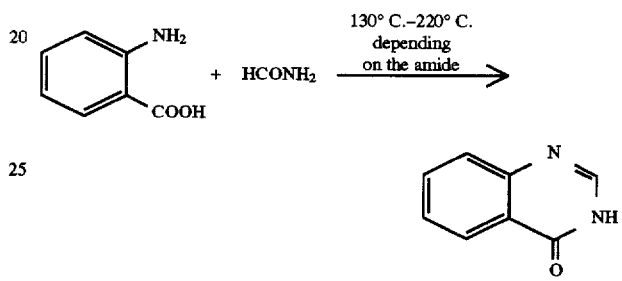

This reaction suffers from high temperature conditions, and the yields generally decrease as the molecular weight of the amide increases, leading to extensive decarboxylation. To avoid extensive thermal decarboxylation of the anthranilic acid, esters of anthranilic acids have been utilized, requiring higher temperatures and longer reaction times. A thioamide version of the Niementowski's synthesis has also been introduced with limited success.

A variation of the Niementowski synthesis involves condensation of an anthranilic acid amide with ethyl orthoformate. It suffers from lack of generality and unavailability of higher analogs of the orthoformate ester.

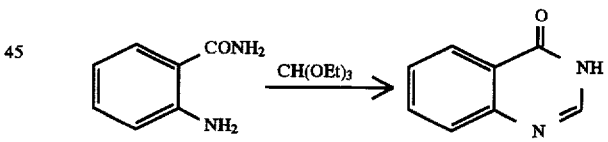

Condensation of an amide with anthranilic acid ester in the presence of a dehydrating agent (e.g. POCl₃, SOCl₂ or COCl₂) also produces quinazolones in good yield. Sensitive functionalities are not tolerated under these conditions.

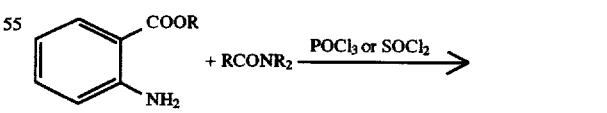

2. Cyclization of o-amidobenzamides: Heating the ammonium salts of o-amidobenzoates at a high temperature, preferably in a sealed tube, produces 4-quinazolones via elimination of water.

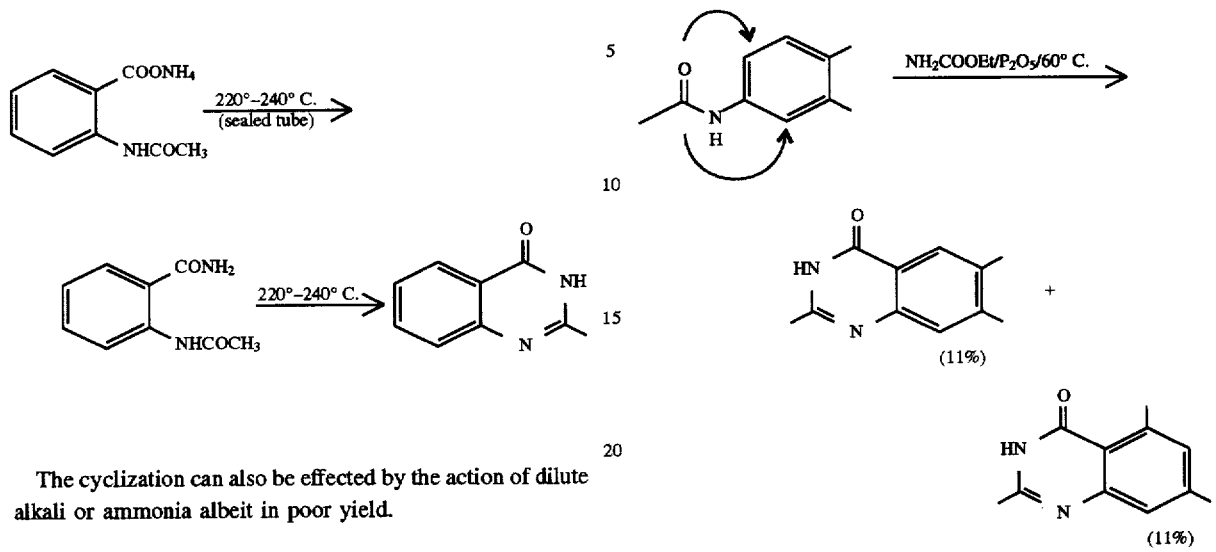

The cyclization can also be effected by the action of dilute alkali or ammonia albeit in poor yield.

3. From o-aminobenzonitriles. o-Aminobenzonitriles, on treatment with $H_2O_2$/NaOH produce 4-quinazolones via the intermediate amide. Sensitive functionalities are not usually tolerated under the harsh oxidative hydrolysis conditions.

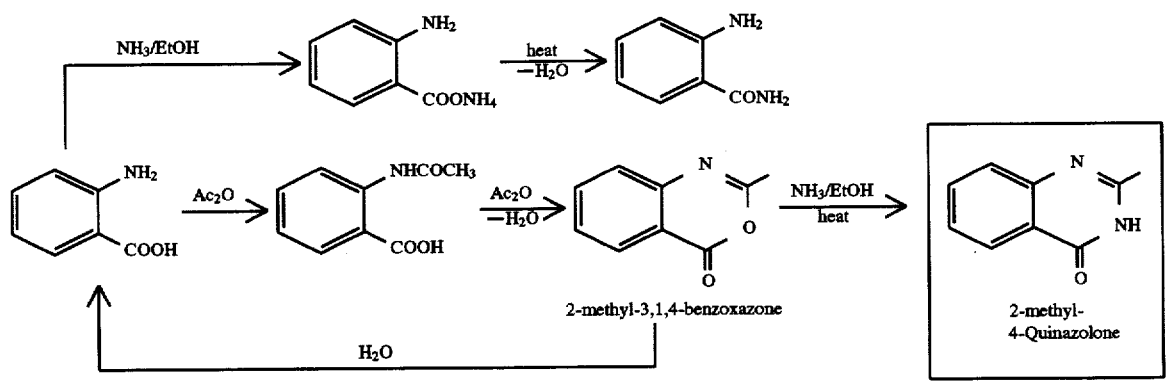

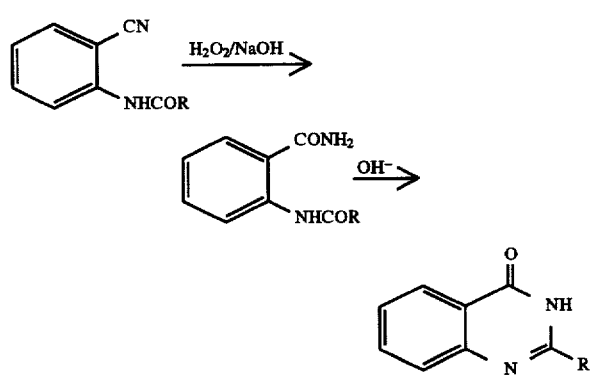

4. From acetanilide. Acetanilide reacts with ethyl carbamate in the presence of phosphorous pentoxide to produce 4-quinazolone. For unsymmetrical 4-quinazolones this reaction produces a mixture of regioisomers, thereby complicating the isolation and lowering the yield.

5. From acylanthranil (3,1,4-Benzoxazone). Heating anthranilic acid in a large excess of acid anhydride (e.g. acetic anhydride) produces 3,1,4-benzoxazone. Complete removal of acid anhydride to dryness followed by treatment with ammonia (or an amine) in an alcoholic medium gives rise to quinazolones.

This method, although providing a means for the production of 4-quinazolone derivatives, suffers from the following disadvantages:

1. Complete removal of acetic anhydride to drness, necessary for the process to be successful, is difficult to perform in production scale. 2. The intermediate benzoxazone is extremely moisture sensitive; water present even in trace amounts hydrolyzes the benzoxazone to the starting anthranilic acid which upon further treatment with ammonia during the process is converted to the ammonium salt and eventually to the corresponding amide thereby complicating the isolation/purification of the quinazolone and also lowering the yield in the process. Complete exclusion of moisture, a crucial requirement for the alcoholic aminolysis step, is also difficult to achieve in a production scale.

A process to prepare 4-quinazolones which circumvents these critical deficiencies and is also amenable to large scale synthesis will be highly desirable. The present invention thus provides a simple, efficient one-pot conversion of anthranilic acids to 4-quinazolones which obviates the problems associated with the current technologies.

DESCRIPTION OF THE PRIOR ART

The following prior art references are disclosed in accordance with the terms of 37 CFR 1.56, 1.97, and 1.93.

U.S. Pat. No. 3,714,354 discloses a process of producing bronchial dilation which comprises administering to a subject an effective amount of a substituted quinazoline carboxylic acid ester.

U.S. Pat. No. 3,793,326 discloses 6,7-disubstituted-quinazolinones useful as analgesic and tranquilizer agents.

U.S. Pat. No. 4,695,569 discloses bicyclic heterocyclyl containing N-(bicyclic heterocyclyl-4-piperidinamines having antihistaminic and serotonin-antagonistic properties which compounds are useful agents in the treatment of allergic diseases.

U.S. Pat. No. 4,981,856 discloses quinazoline derivatives which possess anti-tumor activity.

U.S. Pat. No. 5,025,014 discloses the same compounds as U.S. Pat. No. 4,695,569 but which are useful agents in the treatment of allergic diseases.

U.S. Pat. No. 5,126,339 discloses the same compounds as U.S. Pat. No. 4,695,569 and U.S. Pat. No. 5,025,014 and which are also useful agents in the treatment of allergic diseases.

WO 93/21163 (International Publication Number) dated 28 Oct. 1993 (PCT publication) discloses quinazolones having cardiovascular activity.

Other references pertinent to quinazolines include:

1. Levin, J. L.; Chan, P. S.; Porter, R. S., *Drugs of the Future*, 1995, 20 (4):371–375.
2. Peach, M. J., *Molecular Actions of Angiotensin. Biochom Pharmacol*, 1981, 30, 2745.
3. Buhlmayer, P. Angiotensin-II antagonist: Patent activity since the discovery of DuP-753. *Curr Opin Ther Pat* 1992, 2: 1693.
4. Dudley, D. T.; Hamby, J. M., Recent Advances in Angiotensin II receptor antagonists. *Curr Opin Ther Pat* 1993, 3, 581.
5. Armarego, W. L. F., Fused Pyrimidines, Part I Quinazolines, Interscience Publishers, 1967, pp 75–217.
6. Williamson, T. A., *The Chemistry of Quinazolones, Heterocyclic Compounds*, Volume 6, Edited by Elderfield; John Wiley Editions, 1957, pp 324–376.
7. Niementowski, *J. Pract. Chem.*, 1961, 11, 70.
8. Armarego, *J. Appl. Chem.*, 1961, 11, 70. (Also see, J. Org. Chem., 1976, 41, 838).
9. Meyer and Wagner, *J. Org. Chem.*, 1943, 8, 239.
10. Sen and Gupta, *J. Indian Chem Soc.*, 1962, 39, 368.
11. McKee, McKee and Bost, *J. Am. Chem. Soc*, 1947, 69, 184.
12. Bogert and Steiner, *J. Am. Chem. Soc.*, 1905, 27, 1327.
13. Boger and Hand, *J. Am. Chem. Soc.*, 1902, 24, 1031.
14. Boger and Hand, *J. Am. Chem. Soc.*, 1903, 25, 935.
15. Mckee, Mckee and Bost, *J. Am. Chem. Soc.*, 1946, 68, 1902.
16. Taylor, Knopf and Borror, *J. Am. Chem. Soc.*, 1960, 82, 3152.
17. Bogert and Seil, *J. Am. Chem. Soc.*, 1905, 27, 1305.
18. Brandstorm and Carlsson., *Acta Chimica Scandinavia*, 1967, 21, 983.
19. Wheeler, A. S., Constable, E. W., *J. Am. Chem. Soc.*, 1923, 45, 1999.
20. Valentine, D., Jr.; Tilley J. W.; LeMahieu, R. A. *J. Org. Chem.*, 1981, 46, 4614.

All of the above cited prior art and any other references mentioned herein are incorporated herein by reference in their entirety.

SUMMARY OF THE INVENTION

The present invention provides a process for preparing a quinazolone which comprises the steps of (a) dehydrating a N-acyl beta amino acid (such as an anthranilic acid) in the presence of a dehydration agent and an organic solvent for a sufficient period of time and under suitable temperature and pressure conditions to form an oxazone (b) adding a carboxylic acid and a primary amine salt of a carboxylic acid to said oxazone to form a mixture, (c) distilling azeotropically said mixture for a suitable period of time and suitable temperature and pressure conditions to substantially remove said dehydration agent and said organic solvent, and (d) heating the product of step (c) for a sufficient period of time and under suitable temperature and pressure conditions to form said quinazolone.

DETAILED DESCRIPTION OF THE INVENTION

The present invention thus provides a novel process for preparing quinazolones which overcomes the prior deficiencies mentioned above. Specifically there is provided a process for preparing a quinazolone which comprises the steps of (a) dehydrating a N-acyl beta amino acid in the presence of a dehydration agent and an organic solvent for a sufficient period of time and under suitable temperature and pressure conditions to form an oxazone (b) adding a carboxylic acid and a primary amine salt of a carboxylic acid to said oxazone to form a mixture, (c) distilling azeotropically said mixture for a suitable period of time and under suitable temperature and pressure conditions to substantially remove said dehydration agent and said organic solvent, and (d) heating the product of step (c) for a sufficient period of time and under suitable temperature and pressure conditions to form said quinazolone.

The starting materials of the present invention process are N-acyl beta amino acids (such as N-acyl anthranilic acids) which have the general formula

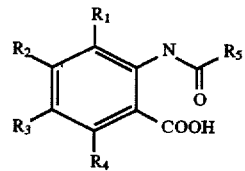

I wherein (a) $R_1$, $R_2$, $R_3$, and $R_4$ are each independently selected form the group consisting of hydrogen, halogen, alkoxy, alkyl, hydroxy, nitro and aryl; (b) $R_1$ and $R_2$, $R_2$ and $R_3$, and $R_3$ and $R_4$ may also (in addition to the above) form a cyclic ring containing a total of 2 to 6 atoms selected from the group consisting of carbon atoms, oxygen atoms, nitrogen atoms, sulfur atoms, and mixtures thereof, with the proviso that said ring can be substituted or unsubstituted; and (c) $R_5$ is selected from the group consisting of hydrogen, unsubstituted alkyl, substituted alkyl, unsubstituted aryl and substituted aryl.

These amino acids are commercially available.

The quinazolones being prepared have the general formula

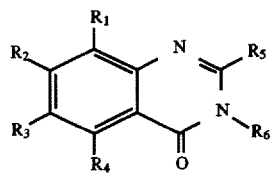

II wherein $R_1$, $R_2$, $R_3$, $R_4$ and $R_5$ are the same as set forth above in formula I, and $R_6$ is selected from the group consisting of substituted alkyl, unsubstituted alkyl, substituted aryl and unsubstituted aryl.

In the above definitions of $R_1$-$R_6$, the term halogen includes chlorine, fluorine, bromine and iodine. The term alkyl includes straight and branch chained saturated hydrocarbon radicals having from 1 to 20 carbon atoms such as, for example, methyl; ethyl; 1-methylethyl; 1,1-dimethylethyl; propyl; 2-methylpropyl; butyl; pentyl; hexyl and the like. The term alkoxy includes the alkyl definition above plus the oxygen atom, e.g. methoxy, ethoxy, isopropoxy, tert-butoxy, and the like. The term aryl includes phenyl, naphthyl, anthryl, phenanthyl and the like.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described hereinabove. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms. This invention is not intended to be limited in any manner by the permissible substituents of organic compounds.

Typical quinazolones that can be prepared by the novel processes of the present invention include without limitation, the compounds having the following formulae:

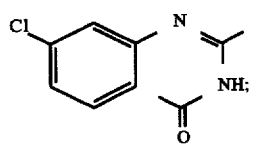

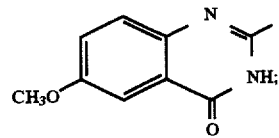

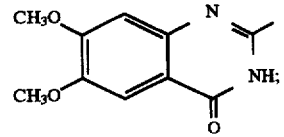

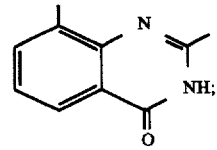

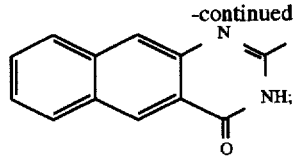

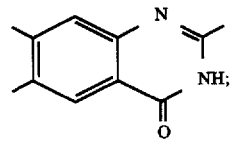

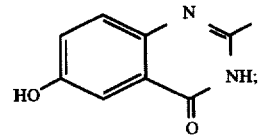

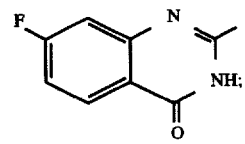

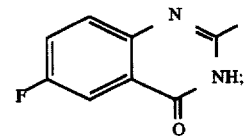

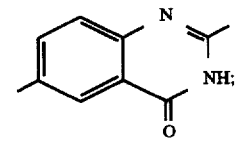

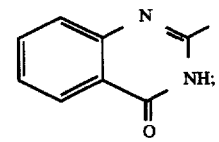

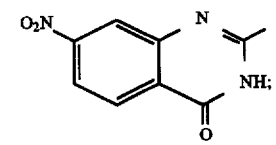

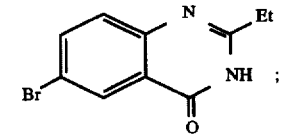

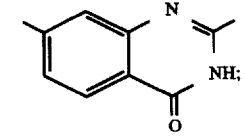

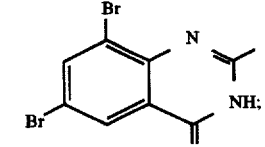

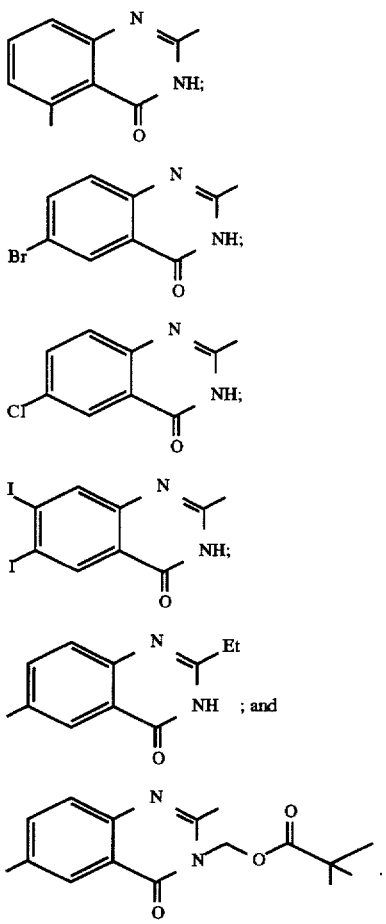

The above 21 formulae correspond to Examples 5–25 set forth hereinafter.

In step (a) of the present invention process, the N-acyl beta amino acid is subject to dehydration in the presence of a dehydration agent and an organic solvent at a temperature of from about 0° C. to about 300° C., preferably from about 75° C. to about 200° C. The reaction time is not critical and generally is accomplished in about 1 minute to about 24 hours. The reaction pressure is not critical and can be atmospheric, sub-atmospheric or super-atmospheric. Under these conditions, the end product is an oxazone having the general formula

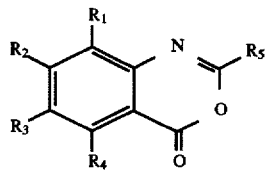

wherein $R_1$–$R_5$ have the same designations as set forth above.

The dehydration agent employed in the present invention process is any material which removes water from the N-acyl beta amino acid (e.g. N-acyl anthranilic acid) in order to form an oxazone. Such agents include without limitation, acid anhydrides of the carboxylic acids, e.g. mixed formic-acetic anhydride, acetic anhydride, propanoic anhydride, butyric anhydride, valeric anhydride, caproic anhydride, heptanoic anhydride, octanoic anhydride, nonanoic anhydride, undecanoic anhydride, isobutyric anhydride, isovaleric anhydride, cyclohexane carboxylic acid anhydride, and mixtures thereof.

The dehydration agent employed can be used in any amount as long as it functions in the desired manner and accomplishes the desired end result. In general, such agent is used in a molar ratio of from about 1:1 to about 5:1, based on one mole of N-acyl beta amino acid. Higher ratios than 5:1 can be used if so desired.

The organic solvent used with the dehydration agent in step (a), is any solvent which functions in a manner to have an azeotropic relationship with the carboxylic acid and the dehydration agent mentioned herein. One such solvent which falls into this category is heptane; another is octane; other higher hydrocarbons can be employed as long as they meet the criteria of providing the azeotropic relationship. The use of this particular type organic solvent is critical to the overall process. The organic solvent employed can be used in any amount as long as it functions in the desired manner and accomplishes the desired end result. In general, the solvent is used in a molar ratio of from about 1:2 to about 20:1, based on one mole of the N-acyl beta amino acid. Higher ratios than 20:1 can be used if so desired.

In step (b) of the present invention process, a carboxylic acid and a primary amine salt of a carboxylic acid are added to said oxazone to form a mixture. This addition and mixing can be accomplished at any temperature and pressure conditions as long as the desired end result is obtained. In general, such temperature is from about 0° C. to about 50° C., preferably from about 20° C. to about 40° C.

The carboxylic acid employed in the present invention is used as a second solvent and is employed as such to assist in the azeotropic distillation [with the organic solvent in step (a)] to remove the dehydration agent. It is critical to remove the dehydration agent in order to convert the oxazone to the quinazolone.

The carboxylic acid employed includes, without limitation, formic acid, acetic acid, propanoic acid, butyric acid, valeric acid, caproic acid, heptanoic acid, octanoic acid, nonanoic acid, undecanoic acid, isobutyric acid, isovaleric acid, cyclohexanone carboxylic acid, and mixtures thereof.

The carboxylic acid employed can be used in any amount as long as it functions in the desired manner and accomplishes the desired end result. In general, such acid is used in a molar ratio of 1:1 to about 20:1, based on one mole ratio of oxazone. Higher ratios than 20:1 can be used if so desired.

The primary amine salt of a carboxylic acid has the general formula $$R_6NH_3^+ \cdot RCOO^- \qquad \text{IV}$$

wherein $R_6$ is the same as set forth above in Formula II. R is hydrogen or alkyl ($C_1$–$C_{20}$), or mixtures thereof.

In step (c) of the present invention process, the resultant mixture from step (b) is subjected to azeotropic distillation in order to remove or substantially remove the residual dehydration agent from said mixture. As previously, mentioned, it is critical that said agent remaining be removed in order that the oxazone can be converted to the quinazolone.

Such distillation can be conducted under any temperature, pressure and time conditions as long as the desired end result is achieved. In general, such temperatures are from about 70° C. to about 300° C.

In step (d) of the present invention process, the resultant product of step (c) is heated, generally under reflux in a carboxylic acid medium, for a sufficient period of time and under suitable temperature and pressure conditions to form said quinazolone. The heating conditions of temperature, pressure and time are not critical as long as the desired end result is achieved. In general, the temperature is from about 0° C. to about 300° C., preferably from about 100° C. to about 200° C.

In one embodiment of the present invention, the preparation of 4-quinazolones from N-acetylanthranilic acids can be typified by the synthesis 2,6,7-trimethyl-4(3H)-quinazolone (7). The synthesis of 4-quinazolone (7) was efficiently accomplished by a sequence involving acetic anhydride promoted ring closure of the N-acetylanthranilic acid (4) obtained after the Pd-catalyzed carboxylation in Scheme 2, to the corresponding benzoxazone (6) followed by ammonolysis of the benzoxazone (6) with ammonium acetate in acetic acid producing the corresponding 2,6,7-trimethyl-4(3H)-quinazolone (7) in 80% yield (Scheme 3).

Anthranilic acid (5), instead of N-acylanthranilic acid (4), can also function as the starting material whereby it gets acylated first in situ to the N-acetylanthranilic acid (4), consuming an extra equivalent of acetic anhydride, prior to the benzoxazone formation.

2,6,7-Trimethyl-3,1,4-benzoxazone was readily prepared by treating the corresponding N-acetyl anthranilic acid with acetic anhydride (1.4 eq) in heptane (reflux, 3 h). Ammonium acetate (5 eq per mol of substrate) was added to the reaction mixture and the residual acetic anhydride was removed by azeotropic distillation of heptane under atmospheric pressure. Removal of any residual acetic anhydride is crucial in order for the next step, the ammonolysis of the benzoxazone, to be successful. Acetic acid was then added to the reaction mixture and heptane was subsequently replaced by acetic acid via azeotropic distillation. (Direct displacement of acetic anhydride (bp 140° C.) to acetic acid (bp 116° C.) by distillation is not possible. Therefore, such solvent displacement becomes only feasible by azeotropic distillation with the intervention of a third solvent, e.g. heptane (bp 98° C.), which forms a binary azeotrope with both acetic anhydride and acetic acid). The mixture was refluxed for 12 hours at the end of which quinazolone formation was complete as indicated by HPLC analysis. The product 4-quinazolone (7) was isolated by adding water to the reaction mixture in consistently high yields (80%).

After the Pd-catalyzed carbonylation reaction in Scheme 1, care should be exercised to remove any unreacted starting material, namely the 2-bromoacetanilide, from the product 2-acetylaminobenzoic acid (by acid-base extraction) before it is subjected to the above synthetic protocol in Scheme 3. Any unreacted 2-bromoacetanilide which is carried forward reacts under ammonium acetate-acetic acid conditions forming the corresponding amidine and water. The water formed hydrolyzes the 4-benzoxazone to the starting anthranilic acid which upon further treatment with ammonia during the process is converted to the ammonium salt and eventually to the corresponding amide, thereby complicating the isolation/ purification of the quinazolone and also lowering the yield in the process (Scheme 4).

These synthetic conditions were successfully applied to prepare a diverse spectrum of 4-quinazolone analogs from a representative group of anthranilic acids and acid anhydrides (Table 1—Examples 5–25 herein). In each case the product was characterized by $^1$H and $^{13}$C NMR.

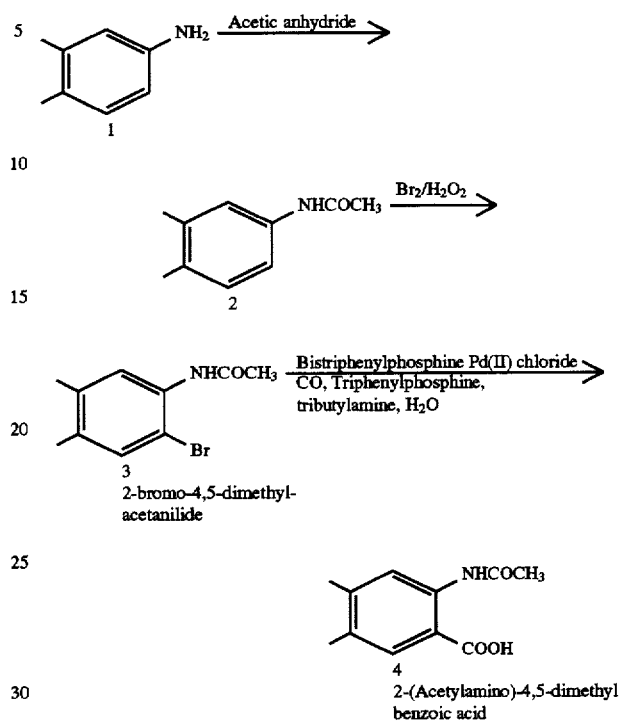

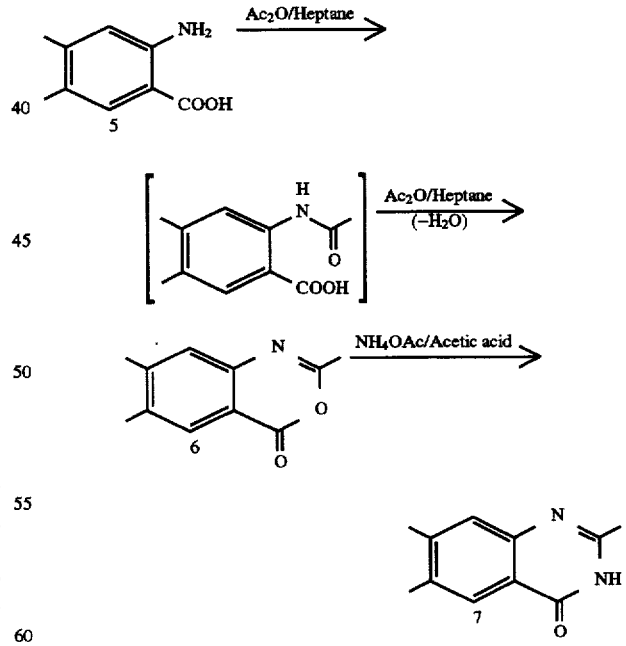

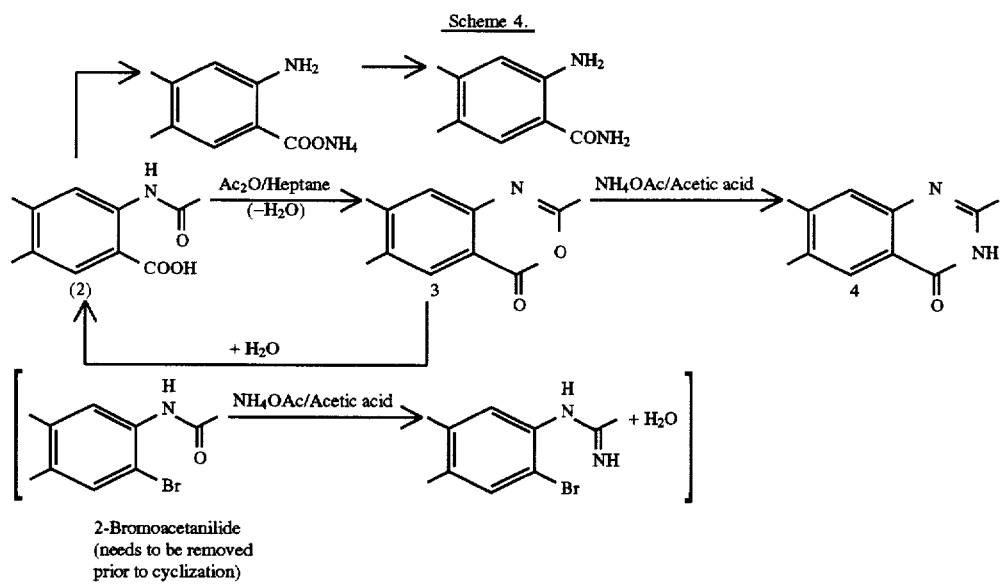

Scheme 4.

2-Bromoacetanilide
(needs to be removed
prior to cyclization)

The following specific examples are supplied for the purpose of better illustrating the invention. These examples are not intended, however, to limit or restrict the scope of the invention in any way and should not be construed as providing conditions, parameters, or values which must be utilized exclusively in order to practice the present invention.

EXAMPLE 1
Preparation of 2-Bromo-4,5-dimethylacetanilide

To a stirred solution of 50.0 g (0.41 mol) of 3,4-dimethylaniline in 250 mL of glacial acetic acid was added 46.0 g (0.45 mol) of acetic anhydride was added dropwise with ice-bath cooling. The reaction was heated for 15 minutes at 120° C., then cooled to 10° C. Bromine (32.8 g, 0.21 mol) was added dropwise over 25 minutes. The addition funnel was washed with a small amount of acetic acid, and 27.2 g (0.24 mol) of 30% hydrogen peroxide was added over 30 minutes. The reaction was stirred for 2 hours at 10°–15° C. and then poured into 1200 mL of cold water. The precipitated product was collected by filtration, washed with water, and dried under vacuum to give 93.0 g (94% yield) of crude 2-bromo-4,5-dimethylacetanilide which was used without further purification.

EXAMPLE 2
Preparation of 2-(Acetylamino)-4,5-dimethylbenzoic acid

A 1 L autoclave was charged with 72.6 g (0.30 mol) of 2-bromo-4,5-dimethylacetanilide, 0.30 g of bis(triphenylphosphine)palladium(II) chloride, 1.5 g triphenylphosphine, 18 mL of water, 79 mL of tributylamine, and 375 mL of toluene, and the unit was purged with nitrogen. Stirring was begun, and the vessel was then pressured to 200 psig with nitrogen to test for system leaks. When no leaks were found, the nitrogen was vented, and the vessel was pressured to 50 psig with carbon monoxide and heated at 120° C. (pressure now 70 psig). When the CO in the system was depleted, additional CO was charged as needed from a reservoir until the pressure drop ceased, indicating the end of the reaction. After cooling to room temperature, the vessel was vented and the reaction mixture removed from the autoclave. The mixture was cooled to 10° C., and the solids which formed were removed by filtration. The solids were added to 30 mL of water, acidified with 10% HCl, cooled to 10° C., and filtered. The mother liquor was added to 50 mL of water and basified with 10% NaOH. The aqueous layer was separated, acidified with 10% HCl, cooled to 10° C., and filtered. The combined solids were dried under vacuum to give 51.1 g (82%) of crude 2-(acetylamino)-4,5-dimethylbenzoic acid.

EXAMPLE 3
Synthesis of 2,6,7-trimethyl-4(3H)-quinazolinone from 2-(Acetylamino)-4,5-dimethylbenzoic acid A mixture of 2-acetylamino-4,5-dimethylbenzoic acid (30.22 g, 145 mM), acetic acid anhydride (20.35 g, 200 mM) and heptane (67.87 g, 100 mL) was heated to reflux for three hours at the end of which complete disappearance of starting material and formation of benzoxazone was observed by HPLC analysis. Ammonium acetate (50.2 g, 651 mM) was added and the mixture was distilled under atmospheric pressure. Approximately 60 mL of heptane was collected via distillation. Acetic acid (150 mL) was added and the distillation was continued till approximately another 110 mL distillate was collected. (overhead temperature: 116° C. and the batch temperature: 140° C.). The mixture was heated to reflux for 12 hours at the end of which complete disappearance of the benzoxazone and formation of quinazolone was observed by HPLC analysis. The mixture was cooled to room temperature; crystallization occurred. Water (160 mL) was added and the mixture was cooled to 4°–6° C. (ice-water cooling) and stirred at 4°–6° C. for two hours. The crystals were filtered, washed with water and dried under vacuum for 10 hours (60° C.) to produce 21.5 g of the desired quinazolinone (80% yield).

EXAMPLE 4
Synthesis of 2,6,7-trimethyl-4(3H)-quinazolinone from 2-amino-4,5-dimethylbenzoic acid A mixture of 2-amino-4,5-dimethylbenzoic acid (30.22 g, 183 mM), acetic anhydride (55.96 g, 550 mM) and heptane (67.87 g, 100 mL) was heated to reflux for three hours at the end of which complete disappearance of starting material and formation of benzoxazone was observed by HPLC analysis. Ammonium acetate (50.2 g, 651 mM) was added and the mixture was distilled under atmospheric pressure. Approximately 60 mL of heptane was collected via distillation. Acetic acid (150 mL) was added and the distillation was continued till approximately another 110 mL distillate was collected (overhead temperature: 116° C. and the batch temperature: 140° C.). The mixture was heated to reflux for 12 hours at the end of which complete disappearance of the benzoxazone and formation of quinazolone was observed by HPLC analysis. The mixture was cooled to room temperature; crystallization occurred. Water (160 mL) was added and the mixture was cooled to 4°–6° C. (ice-water cooling) and stirred at 4°–6° C. for two hours. The crystals were filtered, washed with water and dried under vacuum for 10 hours (60° C.) to produce 21.5 g of the desired quinazolinone (80% yield).

EXAMPLES 5–25

Example 4 was repeated twenty-one (21) times using the same procedure but using different starting materials, i.e. anthranilic acids and acid anhydrides. In each case, the end product (quinazolone) was characterized by $^1$H and $^{13}$C NMR. The results of these twenty-one examples are shown in Table I.

thereof, with the proviso that said ring can be substituted or unsubstituted; and (c) $R_3$ is selected from the group consisting of hydrogen, unsubstituted alkyl, substituted alkyl, unsubstituted aryl and substituted aryl; and (d) $R_4$ is selected from the group consisting of substituted and unsubstituted alkyl and aryl.

The starting materials which are subjected to the dehydration steps are N-acyl beta amino acids which, in this case, have the general formula

VI wherein (a) $R_1$ and $R_2$ are each independently selected from the group consisting of hydrogen, halogen, alkoxy, alkyl, hydroxy, nitro and aryl; (b) $R_1$ and $R_2$ may also (in addition

TABLE I

Quinazolone (end product) formula

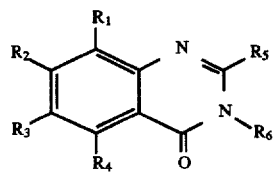

II

| Example | $R_1$ | $R_2$ | $R_3$ | $R_4$ | $R_5$ | $R_6$ | Yield |
|---|---|---|---|---|---|---|---|
| 5 | H | Cl | H | H | $CH_3$ | H | 81.0 |
| 6 | H | F | H | H | $CH_3$ | H | 84.0 |
| 7 | H | H | Br | H | $CH_3$ | H | 85.0 |
| 8 | H | H | $OCH_3$ | H | $CH_3$ | H | 83.0 |
| 9 | H | H | F | H | $CH_3$ | H | 88.0 |
| 10 | H | H | H | $CH_3$ | $CH_3$ | H | 91.0 |
| 11 | H | $OCH_3$ | $OCH_3$ | H | $CH_3$ | H | 82.0 |
| 12 | H | H | $CH_3$ | H | $CH_3$ | H | 87.0 |
| 13 | H | H | Br | H | $CH_3$ | H | 80.0 |
| 14 | $CH_3$ | H | H | H | $CH_3$ | H | 90.0 |
| 15 | H | H | H | H | $CH_3$ | H | 92.0 |
| 16 | H | H | Cl | H | $CH_3$ | H | 81.0 |
| 17 | H | [cyclic $C_4H_4$] | | H | $CH_3$ | H | 90.0 |
| 18 | H | $NO_2$ | H | H | $CH_3$ | H | 78.0 |
| 19 | H | I | I | H | $CH_3$ | H | 66.0 |
| 20 | H | $CH_3$ | $CH_3$ | H | $CH_3$ | H | 94.0 |
| 21 | H | H | Br | H | $C_2H_5$ | H | 85.0 |
| 22 | H | H | $CH_3$ | H | $C_2H_5$ | H | 92.0 |
| 23 | H | H | OH | H | $CH_3$ | H | 45.0 |
| 24 | H | $CH_3$ | H | H | $CH_3$ | H | 82.0 |
| 25 | H | $CH_3$ | H | H | $CH_3$ | $CH_2OC(O)C(CH_3)_3$ | 80.0 |

In another facet of the present invention, it has also been found that 5,6-dihydro-3H-pyrimidin-4-one derivatives ("pyrimidin") can be prepared by the same process as set forth above relating to the preparation of quinazolones. These pyrimidin compounds have the general formula

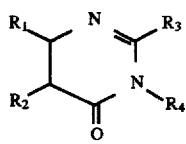

V wherein (a) $R_1$ and $R_2$ are each independently selected from the group consisting of hydrogen, halogen, alkoxy, alkyl, hydroxy, nitro and aryl; (b) $R_1$ and $R_2$ may also (in addition to the above) form a cyclic ring containing a total of 2 to 6 atoms selected from the group consisting of carbon atoms, oxygen atoms, nitrogen atoms, sulfur atoms, and mixtures thereof, with the proviso that said ring can be substituted or unsubstituted; and (c) $R_3$ is selected from the group consisting of hydrogen, unsubstituted alkyl, substituted alkyl, unsubstituted aryl and substituted aryl.

In this facet of the present invention then there is provided a process for preparing a 5,6-dihydro-3H-pyrimidin-4-one derivatives which comprises the steps of (a) dehydrating a N-acyl beta amino acid in the presence of a dehydration agent and an organic solvent for a sufficient period of time and under suitable temperature and pressure conditions to form an oxazone (b) adding a carboxylic acid and a primary amine salt of a carboxylic acid to said oxazone to form a mixture, (c) distilling azeotropically said mixture for a suitable period of time and under suitable temperature and pressure conditions to substantially remove said dehydration agent and said organic solvent, and (d) heating the product of step (c) for a sufficient period of time and under suitable temperature and pressure conditions form said pyrimidin.

All the temperature, pressure and time conditions set forth above are the same for the preparation of the pyrimidins.

In a third facet of the present invention, it has been found that the anthranilic acids which are used in the preparation of the quinazolones can be prepared by a novel process which is more efficient than the prior art processes. Specifically, this new invention provides a process for preparing an anthranilic acid which comprises the steps of (a) acylating an aniline derivative to form the corresponding acylated product, (b) subjecting said acetylated product to halogenation conditions in the presence of an oxidizing agent to form a halogenated product, and (c) subjecting said halogenated product to carbonylation conditions including suitable temperature and pressure to form said anthranilic acid. An example of this novel process is disclosed above in Scheme 1.

The anthranilic acids have the formula

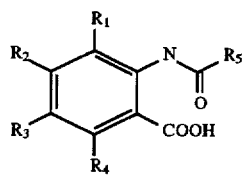

I wherein (a) $R_1$, $R_2$, $R_3$, and $R_4$ are each independently selected from the group consisting of hydrogen, halogen, alkoxy, alkyl, hydroxy, nitro and aryl; (b) $R_1$ and $R_2$, $R_2$ and $R_3$, and $R_3$ and $R_4$ may also (in addition to the above) form a cyclic ring containing a total of 2 to 6 atoms selected from the group consisting of carbon atoms, oxygen atoms, nitrogen atoms, sulfur atoms, and mixtures thereof, with the proviso that said ring can be substituted or unsubstituted; and (c) $R_5$ is selected from the group consisting of hydrogen, unsubstituted alkyl, substituted alkyl, unsubstituted aryl and substituted aryl.

The starting materials in this new process are the aniline derivatives which have the formula

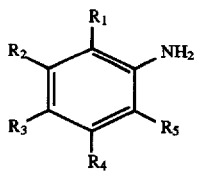

VII wherein (a) $R_1$, $R_2$, $R_3$, and $R_4$ are each independently selected from the group consisting of hydrogen, halogen, alkoxy, alkyl, hydroxy, nitro and aryl; (b) $R_1$ and $R_2$, $R_2$ and $R_3$, and $R_3$ and $R_4$ may also (in addition to the above) form a cyclic ring containing a total of 2 to 6 atoms selected from the group consisting of carbon atoms, oxygen atoms, nitrogen atoms, sulfur atoms, and mixtures thereof, with the proviso that said ring can be substituted or unsubstituted; and (c) $R_5$ is selected from the group consisting of hydrogen, unsubstituted alkyl, substituted alkyl, unsubstituted aryl and substituted aryl.

In this third inventive process, the acylation conditions of step (a) encompass the use of an acylation agent such as an anhydride of a carboxylic acid, such as those previously mentioned, e.g. acetic anhydride. The temperatures employed are from about 0° C. to about 200° C., although higher temperatures can be used as long as the desired end result is obtained. Pressure and time of reaction are not critical features. In general, the amount of acylation agent used is in a molar ratio of at least about 1:1 to about 5:1 based on one mole of the aniline derivative.

In the halogenation [step (b)] such conditions include subjecting the acylated product from step (a) to a halogen (Cl, F, Br, or I) containing material in the presence of an oxidizing agent under suitable conditions of temperature, pressure and time to form a halogenated product. The temperatures of this reaction are generally in the range of from about 0° C. to about 250° C. The pressure and time of reaction are not critical. The amount of halogen employed is at least about 1:1 (molar ratio) based on one mole of acylated product being processed. The oxidizing agent is any material which will facilitate an oxidizing reaction and includes, without limitation, organic peroxides (ROOR where R is an alkyl $C_1$–$C_{20}$ group) and $H_2O_2$. The amount employed is at least about 1:1 (molar ratio) based on the acylated product being processed; preferably the ratio is from about 1:1 to about 20:1.

In the carbonylation step (c), the halogenated product from step (b) is subjected to a carbonylation procedure in order to produce the anthranilic acid. The carbonylation is carried out at temperatures of from about 10° C. to about 200° C. under suitable pressures and reaction times to form said acid. This carbonylation is obviously carried out with CO or a CO generating material such as syngas and in the presence of (1) a carbonylation catalyst, (2) an organic solvent such as those described herein, and (3) a basic material such as a tertiary amine, alkali metal carbonate, and the like. Typical carbonylation conditions which can be used in this step (c) include those conditions outlined in U.S. Pat. No. 4,981,995 and which is incorporated herein by reference in its entirety.

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

What is claimed is:

1. A process for preparing 5,6-dihydro-3H-pyrimidin-4-one derivatives which comprises the steps of (a) dehydrating a N-acyl beta amino acid in the presence of a dehydration agent and an organic solvent for a sufficient period of time and under suitable temperature and pressure conditions to form an oxazone (b) adding a carboxylic acid and a primary amine salt of a carboxylic acid to said oxazone to form a mixture, (c) distilling azeotropically said mixture for a suitable period of time and under suitable temperature and pressure conditions to substantially remove said dehydration agent and said organic solvent, and (d) heating the product of step (c) for a sufficient period of time and under suitable temperature and pressure conditions to form said pyrimidine derivative.

2. The process as set forth in claim 1 wherein the pyrimidin derivatives have the formula

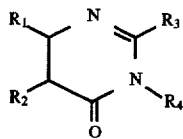

wherein (a) $R_1$ and $R_2$ are each independently selected from the group consisting of hydrogen, halogen, alkoxy, alkyl, hydroxy, nitro and aryl; (b) $R_1$ and $R_2$ may also (in addition to the above) form a cyclic ring containing a total of 2 to 6 atoms selected from the group consisting of carbon atoms, oxygen atoms, nitrogen atoms, sulfur atoms, and mixtures thereof, with the proviso that said ring can be substituted or unsubstituted; and (c) $R_3$ is selected from the group consisting of hydrogen, unsubstituted alkyl, substituted alkyl, unsubstituted aryl and substituted aryl; and (d) $R_4$ is selected from the group consisting of substituted and unsubstituted alkyl and aryl.

3. The process as set forth in claim 1 wherein the N-acyl beta amino acids have the formula

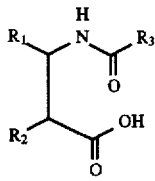

wherein (a) $R_1$ and $R_2$ are each independently selected from the group consisting of hydrogen, halogen, alkoxy, alkyl, hydroxy, nitro and aryl; (b) $R_1$ and $R_2$ may also (in addition to the above) form a cyclic ring containing a total of 2 to 6 atoms selected from the group consisting of carbon atoms, oxygen atoms, nitrogen atoms, sulfur atoms, and mixtures thereof, with the proviso that said ring can be substituted or unsubstituted; and (c) $R_3$ is selected from the group consisting of hydrogen, unsubstituted alkyl, substituted alkyl, unsubstituted aryl and substituted aryl.

4. The process as set forth in claim 1 wherein the dehydration agent is selected from the group consisting of acetic anhydride, propionic anhydride, butyric anhydride, and valeric anhydride.

5. The process as set forth in claim 1 wherein the organic solvent is selected from the group consisting of heptane, octane and other higher hydrocarbons, with the proviso that said organic solvent functions in a manner to have an azeotropic relationship with the carboxylic acid and the dehydrating agent.

6. The process as set forth in claim 1 wherein the carboxylic acid is selected from the group consisting of acetic acid, propionic acid, butyric acid and valeric acid.

7. The process as set forth in claim 1 wherein the dehydration in step (a) is conducted at a temperature of from about 0° C. to about 300° C.

8. The process as set forth in claim 1 wherein the heating in step (d) is conducted at a temperature of from about 0° C. to about 300° C.

9. The process as set forth in claim 1 wherein in step (a) the dehydration agent is used in a molar ratio of from about 1:1 to about 5:1, based on one mole of N-acyl beta amino acid.

10. The process as set forth in claim 1 wherein in step (b), the carboxylic acid is used in a molar ratio of from about 1:1 to about 20:1.

11. The process as set forth in claim 2 wherein step (b), the primary amine salt of a carboxylic acid has the formula

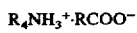

wherein $R_4$ is the same as defined in the pyrimidin formula and R is selected from the group consisting of hydrogen, alkyl $C_1$–$C_{20}$, and mixtures thereof.

* * * * *